(12) United States Patent
Walsh et al.

(10) Patent No.: US 7,284,730 B2
(45) Date of Patent: *Oct. 23, 2007

(54) TRANSDUCER HOLDER

(75) Inventors: Adrienne Walsh, Colorado Springs, CO (US); Maria Campanella, Arlington, VA (US); Sharon Steeves, Bellingham, MA (US)

(73) Assignee: Dale Medical Products, Inc., Plainville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/996,998

(22) Filed: Nov. 24, 2004

(65) Prior Publication Data

US 2005/0137496 A1    Jun. 23, 2005

Related U.S. Application Data

(63) Continuation-in-part of application No. 10/821,337, filed on Apr. 8, 2004.

(60) Provisional application No. 60/461,144, filed on Apr. 9, 2003.

(51) Int. Cl.
    *F16L 3/08*      (2006.01)

(52) U.S. Cl. .................. 248/74.3; 248/205.2; 248/680; 248/74.2; 604/174; 128/877; 128/878; 24/16 R

(58) Field of Classification Search ............ 248/205.2, 248/683, 74.3, 74.2, 68.1, 73; 224/665, 680, 224/682, 683, 684, 901.2, 901.4, 901.8; 128/877, 128/878; 604/174, 179; 24/16 R, 305

See application file for complete search history.

(56) References Cited

U.S. PATENT DOCUMENTS

| | | | |
|---|---|---|---|
| 2,590,006 A | 3/1952 | Gordon | 128/206 |
| 3,046,984 A | 7/1962 | Eby | 128/214 |
| 3,046,989 A | 7/1962 | Hill | 128/348 |
| 3,146,778 A | 9/1964 | Krawiec | 128/349 |
| 3,161,199 A | 12/1964 | Sands | 128/348 |
| 3,255,749 A | 6/1966 | Smithers | 128/169 |
| 3,288,136 A | 11/1966 | Lund | 128/133 |
| 3,430,300 A | 3/1969 | Doan | 24/73 |
| 3,677,250 A | 7/1972 | Thomas | 128/348 |
| 3,786,285 A | 1/1974 | Reibold | 310/8.5 |

(Continued)

FOREIGN PATENT DOCUMENTS

DE      101 15 881 A1      10/2002

(Continued)

OTHER PUBLICATIONS

Anago, "Cath-Control" product brochure.

(Continued)

*Primary Examiner*—Kimberly Wood
(74) *Attorney, Agent, or Firm*—Finnegan, Henderson, Farabow, Garrett & Dunner, L.L.P.

(57) ABSTRACT

System, methods and apparatus are provided for securing one or more transducers to a patient. According to one illustrative embodiment, a transducer holder is provided that includes a base, one or more fasteners for securing one or more transducers, respectively, at least one strap attached to the base for securing the base to the patient, wherein at least two of the fasteners have a different color from one another.

6 Claims, 3 Drawing Sheets

U.S. PATENT DOCUMENTS

| | | | |
|---|---|---|---|
| 3,826,254 A | 7/1974 | Mellor | 128/133 |
| 3,878,849 A | 4/1975 | Muller et al. | 128/349 |
| 3,924,636 A | 12/1975 | Addison | 128/351 |
| 3,927,676 A | 12/1975 | Schultz | 128/351 |
| 3,946,742 A | 3/1976 | Eross | 128/351 |
| 3,977,407 A | 8/1976 | Coleman et al. | 128/348 |
| 4,059,105 A | 11/1977 | Cutruzzula et al. | 128/133 |
| 4,074,397 A | 2/1978 | Rosin | 24/73 |
| 4,088,136 A | 5/1978 | Hasslinger et al. | 128/349 |
| 4,096,863 A | 6/1978 | Kaplan et al. | 128/349 |
| 4,114,626 A | 9/1978 | Beran | 128/348 |
| 4,120,304 A | 10/1978 | Moor | 128/348 |
| 4,122,857 A | 10/1978 | Haerr | 128/348 |
| 4,142,527 A | 3/1979 | Garcia | 128/348 |
| 4,165,748 A | 8/1979 | Johnson | 128/348 |
| 4,215,687 A | 8/1980 | Shaw | 128/169 |
| D260,932 S | 9/1981 | Chodorow et al. | D24/53 |
| 4,308,642 A | 1/1982 | Heyman | 24/306 |
| 4,316,461 A * | 2/1982 | Marais et al. | 604/179 |
| 4,324,237 A | 4/1982 | Buttaravoli | 128/214 |
| 4,331,144 A | 5/1982 | Wapner | 128/207.17 |
| D265,423 S | 7/1982 | Abraham et al. | D24/52 |
| 4,378,012 A | 3/1983 | Brown | 128/207.17 |
| 4,416,664 A | 11/1983 | Womack | 604/174 |
| 4,445,894 A | 5/1984 | Kovacs | 604/179 |
| 4,447,238 A | 5/1984 | Eldridge, Jr. | 604/280 |
| 4,449,527 A | 5/1984 | Hinton | 128/207.17 |
| 4,453,933 A * | 6/1984 | Speaker | 604/179 |
| 4,457,754 A | 7/1984 | Buttaravoli | 604/180 |
| 4,484,913 A | 11/1984 | Swauger | 604/179 |
| 4,490,141 A | 12/1984 | Lacko et al. | 604/180 |
| 4,534,342 A | 8/1985 | Pexa | 128/163 |
| 4,534,762 A | 8/1985 | Heyer | 604/180 |
| 4,548,200 A | 10/1985 | Wapner | 128/207.17 |
| 4,569,348 A | 2/1986 | Hasslinger | 604/179 |
| 4,583,976 A | 4/1986 | Ferguson | 604/174 |
| 4,592,351 A | 6/1986 | Smith et al. | 128/207.17 |
| 4,617,017 A | 10/1986 | Hubbard et al. | 604/179 |
| 4,639,980 A | 2/1987 | Peterson | 24/306 |
| 4,655,209 A | 4/1987 | Scott | 128/156 |
| 4,662,366 A | 5/1987 | Tari | 128/134 |
| 4,665,566 A | 5/1987 | Garrow | 2/171 |
| 4,671,787 A | 6/1987 | Widman | 604/179 |
| 4,702,736 A | 10/1987 | Kalt et al. | 604/180 |
| 4,706,662 A | 11/1987 | Thompson | 128/155 |
| 4,706,914 A | 11/1987 | Ground | 248/74.3 |
| 4,726,716 A | 2/1988 | McGuire | 604/180 |
| 4,737,143 A | 4/1988 | Russell | 604/180 |
| 4,738,662 A | 4/1988 | Kalt et al. | 604/180 |
| 4,778,448 A | 10/1988 | Meer | 604/54 |
| 4,799,923 A | 1/1989 | Campbell | 604/179 |
| 4,804,374 A | 2/1989 | Laskody | 604/180 |
| 4,821,736 A | 4/1989 | Watson | 128/719 |
| 4,822,342 A | 4/1989 | Brawner | 604/180 |
| 4,823,789 A | 4/1989 | Beisang, III | 128/207.18 |
| 4,826,486 A | 5/1989 | Palsrok et al. | 604/174 |
| 4,838,878 A | 6/1989 | Kalt et al. | 604/180 |
| 4,844,061 A | 7/1989 | Carroll | 128/201 |
| 4,911,698 A | 3/1990 | Wapner | 604/329 |
| 4,932,943 A | 6/1990 | Nowak | 604/180 |
| 4,934,646 A * | 6/1990 | Doyle | 248/309.1 |
| 4,939,818 A | 7/1990 | Hahn | 24/16 |
| D310,721 S | 9/1990 | Beisang, III | D24/49 |
| 4,971,271 A * | 11/1990 | Sularz | 248/68.1 |
| D312,880 S | 12/1990 | Bodai et al. | D24/53 |
| 4,974,593 A | 12/1990 | Ng | 128/639 |
| 4,976,700 A | 12/1990 | Tollini | 604/180 |
| 4,986,815 A | 1/1991 | Schneider | 604/180 |
| 4,988,338 A | 1/1991 | Taylor et al. | 604/180 |
| 4,997,421 A | 3/1991 | Palsrok et al. | 604/174 |
| 4,999,885 A * | 3/1991 | Lee | 24/586.1 |
| 5,015,251 A | 5/1991 | Cherubini | 606/203 |
| 5,019,050 A | 5/1991 | Lynn et al. | 604/179 |
| 5,037,397 A | 8/1991 | Kalt et al. | 604/174 |
| 5,038,778 A | 8/1991 | Lott | 128/207.17 |
| 5,042,477 A | 8/1991 | Lewis | 128/207.17 |
| 5,046,945 A * | 9/1991 | McGowan | 431/344 |
| 5,048,158 A | 9/1991 | Koerner | 24/16 |
| 5,084,026 A * | 1/1992 | Shapiro | 604/179 |
| 5,098,399 A | 3/1992 | Tollini | 604/180 |
| 5,100,393 A | 3/1992 | Johnson | 604/180 |
| 5,104,076 A | 4/1992 | Goodall, Jr. | 248/205.2 |
| D326,916 S | 6/1992 | Briggs, III | D24/189 |
| 5,120,300 A | 6/1992 | Shaw | 602/61 |
| 5,147,322 A | 9/1992 | Bowen et al. | 604/180 |
| 5,156,641 A | 10/1992 | White | 128/207.18 |
| 5,167,050 A | 12/1992 | Korsen | 24/16 |
| 5,172,688 A | 12/1992 | Dillon | 128/207.18 |
| 5,174,483 A | 12/1992 | Moore, IV et al. | 224/250 |
| 5,188,101 A | 2/1993 | Tumolo | 128/207.18 |
| 5,200,245 A | 4/1993 | Brodrick, Jr. | 428/100 |
| 5,214,874 A | 6/1993 | Faulkner | 43/25.2 |
| 5,237,988 A | 8/1993 | McNeese | 128/207.17 |
| 5,261,893 A | 11/1993 | Zamierowski | 604/180 |
| 5,271,745 A | 12/1993 | Fentress et al. | 604/179 |
| 5,284,469 A | 2/1994 | Jasen et al. | 602/17 |
| 5,304,146 A | 4/1994 | Johnson et al. | 604/180 |
| 5,305,742 A | 4/1994 | Styers et al. | 128/207.17 |
| 5,306,233 A | 4/1994 | Glover | 602/41 |
| 5,308,339 A | 5/1994 | Kalt et al. | 604/180 |
| 5,341,802 A | 8/1994 | Calebaugh | 128/207.17 |
| 5,342,317 A | 8/1994 | Claywell | 604/179 |
| 5,352,209 A | 10/1994 | Bird et al. | 604/179 |
| 5,357,952 A | 10/1994 | Schuster et al. | 128/207.17 |
| 5,362,303 A | 11/1994 | Jasen et al. | 602/17 |
| D354,812 S | 1/1995 | Jasen et al. | D24/189 |
| 5,385,281 A * | 1/1995 | Byrd | 224/148.6 |
| 5,395,344 A | 3/1995 | Beisang, III et al. | 604/180 |
| 5,397,639 A | 3/1995 | Tollini | 428/343 |
| 5,411,484 A | 5/1995 | Shattuck | 604/179 |
| 5,433,359 A | 7/1995 | Flowers | 224/222 |
| 5,437,273 A | 8/1995 | Bates et al. | 128/207.17 |
| 5,448,985 A | 9/1995 | Byrd | 128/207.17 |
| 5,451,725 A | 9/1995 | Goldman | 181/131 |
| 5,468,231 A | 11/1995 | Newman et al. | 604/180 |
| 5,480,719 A | 1/1996 | Tollini | 428/345 |
| 5,485,837 A | 1/1996 | Solesbee et al. | 128/207.17 |
| 5,490,504 A | 2/1996 | Vrona et al. | 128/207.17 |
| 5,496,282 A | 3/1996 | Militzer et al. | 604/179 |
| 5,501,216 A | 3/1996 | Byrd | 128/207.17 |
| 5,507,285 A | 4/1996 | Mota | 128/207.17 |
| 5,529,062 A | 6/1996 | Byrd | 128/207.17 |
| 5,535,739 A | 7/1996 | Rapoport et al. | 128/204.23 |
| 5,546,933 A | 8/1996 | Rapoport et al. | 128/204.23 |
| 5,546,938 A | 8/1996 | McKenzie | 128/207.17 |
| 5,551,421 A | 9/1996 | Noureldin et al. | 128/207.17 |
| 5,624,403 A * | 4/1997 | Jaquith | 604/179 |
| 5,638,814 A | 6/1997 | Byrd | 128/207.17 |
| 5,664,581 A | 9/1997 | Ashley | 128/876 |
| 5,671,732 A | 9/1997 | Bowen | 128/207.17 |
| 5,682,881 A | 11/1997 | Winthrop et al. | 128/207.18 |
| 5,685,292 A | 11/1997 | Fenn | 128/200.24 |
| 5,704,916 A | 1/1998 | Byrd | 604/179 |
| 5,709,665 A | 1/1998 | Vergano et al. | 604/174 |
| D393,310 S | 4/1998 | Russo | D24/128 |
| 5,735,822 A | 4/1998 | Steins | 604/179 |
| 5,743,885 A | 4/1998 | Hoerby | 604/180 |
| 5,752,511 A | 5/1998 | Simmons et al. | 128/207.18 |
| 5,755,225 A | 5/1998 | Hutson | 128/207.18 |
| 5,785,690 A | 7/1998 | Newman et al. | 604/180 |
| 5,786,062 A | 7/1998 | Callahan, Jr. et al. | 428/100 |
| 5,795,334 A | 8/1998 | Cochrane, III | 604/174 |
| 5,797,394 A | 8/1998 | Boyd | 128/207.17 |
| 5,797,884 A | 8/1998 | Byrd | 604/180 |

| | | | | |
|---|---|---|---|---|
| 5,803,079 | A | 9/1998 | Rogers et al. | 128/207.14 |
| 5,820,000 | A * | 10/1998 | Timberlake et al. | 224/219 |
| 5,833,663 | A | 11/1998 | Bierman | 604/174 |
| 5,845,643 | A | 12/1998 | Vergano et al. | 128/877 |
| 5,855,307 | A * | 1/1999 | Biddick et al. | 224/267 |
| 5,868,132 | A | 2/1999 | Winthrop et al. | 128/207.14 |
| 5,870,849 | A | 2/1999 | Colson, Jr. | 43/25.2 |
| 5,879,335 | A | 3/1999 | Martinez et al. | 604/179 |
| 5,897,519 | A | 4/1999 | Shesol et al. | 602/79 |
| 5,916,199 | A * | 6/1999 | Miles | 604/174 |
| 5,931,854 | A | 8/1999 | Dillon | 606/204.45 |
| 5,941,856 | A | 8/1999 | Kovacs et al. | 604/179 |
| 6,015,119 | A | 1/2000 | Starchevich | 248/65 |
| 6,032,289 | A * | 3/2000 | Villapiano | 2/102 |
| 6,117,086 | A | 9/2000 | Shulze | 600/488 |
| 6,132,398 | A | 10/2000 | Bierman | 604/174 |
| 6,142,953 | A | 11/2000 | Burton et al. | 600/534 |
| 6,209,765 | B1 * | 4/2001 | King | 224/250 |
| 6,261,277 | B1 | 7/2001 | Osborn, III et al. | 604/385.17 |
| 6,296,164 | B1 | 10/2001 | Russo | 224/602 |
| 6,419,660 | B1 | 7/2002 | Russo | 604/180 |
| 6,689,104 | B2 * | 2/2004 | Bierman | 604/174 |
| 6,843,399 | B2 * | 1/2005 | Garcia | 224/665 |
| 2002/0072656 | A1 | 6/2002 | Vantassel et al. | 600/300 |

FOREIGN PATENT DOCUMENTS

| | | |
|---|---|---|
| EP | 0 637 435 A1 | 2/1994 |
| GB | 2235620 A | 3/1991 |
| GB | 2251796 A | 7/1992 |
| WO | WO97/12552 | 4/1997 |
| WO | WO99/55410 | 11/1999 |

OTHER PUBLICATIONS

Ansley, a division of Struckmeyer, "Ansley Tube Holders" product brochures (one page dated 1993).
A-T Surgical Mfg. Co., Inc., "A-T Nasogastric Tube Holder" product brochure.
Beiersdorf Inc., "Coverlet Adhesive Dressings Hospital Sizes (#1307 Used as N-G Holder)" product brochure (1990).
Dale Medical Products, Inc., "Dale Hug Hospital Utility Grip" product brochures (one sheet dated Jul. 1990).
Deknatel, "Naso-Guard, Nasogastric Tube Holder" product brochure.
E. Med Corporation, "Flexi-Trak Anchoring Device" product brochure.
Genetic Laboratories Wound Care, Inc., "NG Strip Nasal Tube Fastener" product brochure.
Genetic Laboratories Wound Care, Inc., "Catheter & Tube Anchoring Device" product brochure.
Genetic Laboratories Wound Care, Inc., "Cath-Strip, Reclosable Catheter Fastener" product brochures.
Genetics Laboratories Wound Care, Inc., "UC Strip Catheter Tubing Fastener" product brochure.
Hudson, "Infant Nasal CPAP System" product brochure (1989).
Inside Advantage, "Cath-Control" product brochure.
M.C. Johnson Co., Inc., "Cath-Secure Dual Tab Multi-Purpose Tube Holder" product brochures.
M.C. Johnson Co., Inc., "Cath-Secure, The Multi-Purpose Tube Holder" product brochures.
M.C. Johnson Co., Inc., "Cath-Secure, The Multi-Purpose Tube Holder" product brochures (one page dated Oct. 1994).
M.C. Johnson Co., Inc., "NG Secure" product brochure.
Medical Technologies, Inc., "Nasal E.T. Tape Kit" product brochure.
Mor-Mac, Inc., "Tube Guard," product brochures (one page dated Sep. 1987).
Scott Specialties, Inc., "Scott Tube Holders" products brochure.
Tecnol, Inc., "Naso-Gastric Tube Holder" product brochures.
Tecnol, Inc., "Secure-All Tube Holder" product brochures (one page dated 1994).
TNT Moborg International Limited, "Immobilé, Line Control as Easy as 1-2-3" product brochures (one page dated 1995).
TNT Moborg International Limited, "Immobilé, Sterile For Compliant Patent Line Control" product brochure.
Trademark Medical Corpation, "Naso-Gastric Tube Holder without Tape" product brochures.
Transatlantic Handelsgesellschaft Stoupe & Co., mbH, "Transafix Fixing Tapes" product brochure (Sep. 1988).
Zefon Medical Products, "Zefon κ-Lok Universal Securement Devices" product brochure.

* cited by examiner

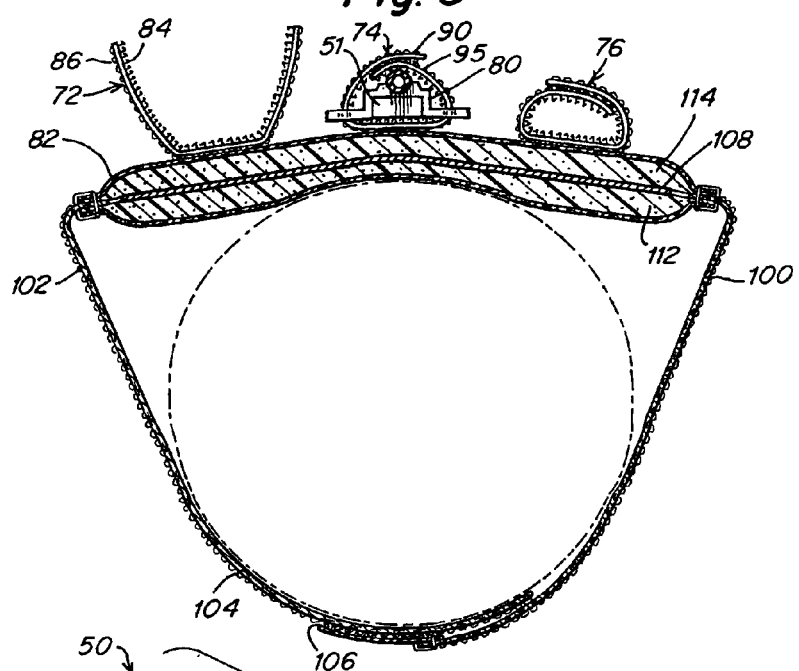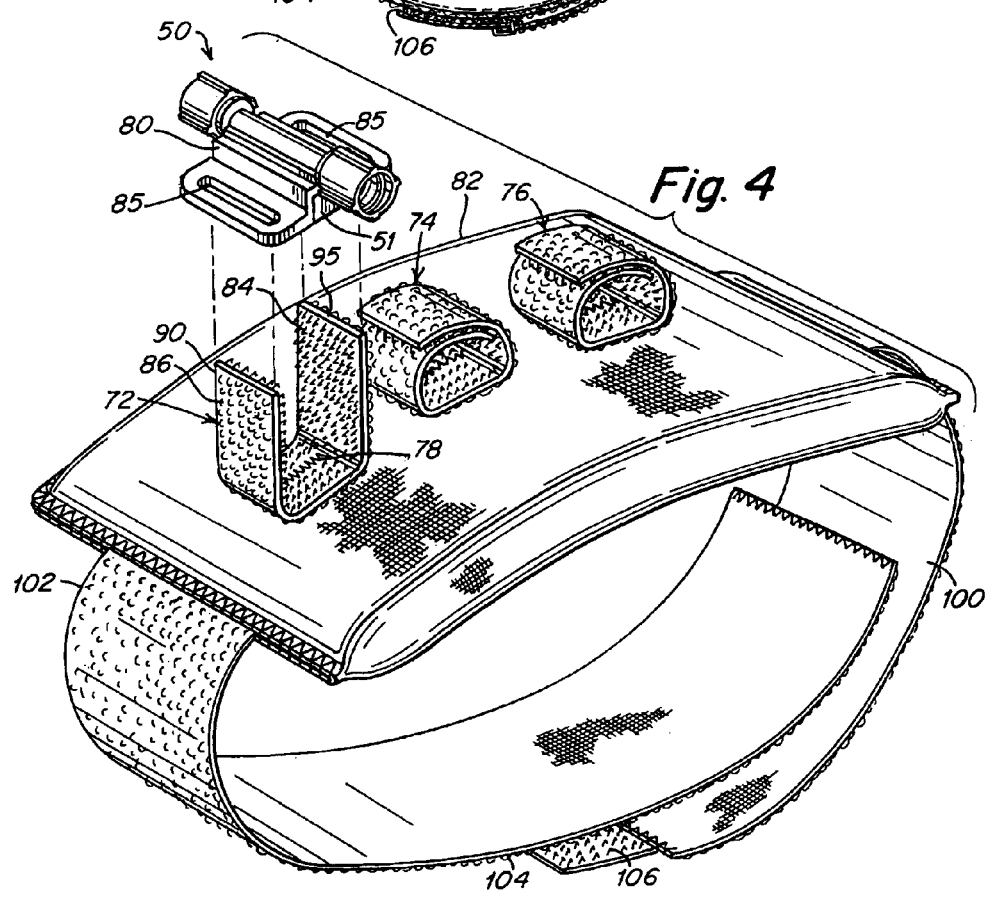

TRANSDUCER HOLDER

This application is a continuation-in-part of U.S. patent application Ser. No. 10/821,337, filed Apr. 8, 2004, which claims the benefit of U.S. Provisional Application No. 60/461,144 filed Apr. 9, 2003, all of which are herein incorporated by reference.

BACKGROUND OF THE INVENTION

Hemodynamic monitoring allows the clinician to have access to information that is not available from a standard assessment of the cardiovascular system. Parameters such as cardiac output (CO) and intracardiac pressures can be directly measured and monitored through an indwelling catheter connected to pressure monitoring equipment. Intracardiac pressures include, among others, pulmonary artery (PA) pressure, radial artery (RA) pressure, and pulmonary capillary wedge pressure (PCWP).

Hemodynamic monitoring systems include one or more indwelling catheters, each connected to a pressure transducer, a flush system, and a bedside monitor. For example, the PA catheter is a multilumen catheter inserted into the pulmonary artery. The arterial catheter, or "A-line," has only one lumen which is used to directly measure arterial blood pressure. Transducers are used to sense vascular pressure in the catheters. A pressure transducer is a small electronic sensor which converts a mechanical pressure (i.e., vascular pressure) into an electrical signal which is displayed on the pressure amplifier or bedside monitor as a continuous waveform with corresponding numerical displays of measurement.

The transducer is typically housed in a plastic connector that also includes a port for connection to an IV solution which is placed in a pressure bag. This allows a slow, continuous infusion of fluid through the vascular catheter. For the transducer to work accurately, the transducer generally must be leveled to the catheter tip. Leveling is the process of aligning the tip of the vascular catheter horizontal to a zero reference position using a stopcock in the pressure tubing close to the transducer. The leveling location is the phlebostatic axis which is located horizontal to the $4^{th}$ intercostal space at the midaxillary line. This coincides most accurately with the atria of the heart.

There are two basic methods for leveling. When the transducer and stopcocks are mounted on a pole close to the bed, the pole height is adjusted to have the stopcock opening level with the catheter tip. To ensure horizontal positioning, a carpenter's level is typically used. The transducer is then "zeroed" to compensate for any distortion by using the stopcock to expose the transducer to air and setting a zero button on the bedside monitor. Each time the bed height or patient position is altered, this leveling procedure is repeated.

Another method for leveling places the transducer and stopcock at the desired location on the chest wall or arm. Ordinary medical tape is used to strap the transducer to the appropriate location on the body to help eliminate the need for repeating the leveling procedure when bed heights are changed. Medical tape, however, can be uncomfortable for the patient, awkward for the caregiver to use, difficult to remove and reapply, can tend to become undone, and increases the likelihood that the caregiver will inaccurately locate the transducer, leading to inaccurate pressure readings.

SUMMARY OF THE INVENTION

System, methods and apparatus are provided for securing one or more transducers to a patient. According to one illustrative embodiment, a transducer holder is provided that includes a base, one or more fasteners for securing one or more transducers, respectively, at least one strap attached to the base for securing the base to the patient, wherein at least two of the fasteners have a different color from one another.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 3 is a cross-sectional view along lines 3-3 of the transducer holder of FIG. 2;

FIG. 4 is a perspective view of the transducer holder of FIGS. 1-3; and

DETAILED DESCRIPTION

Reference will now be made in detail to several illustrative embodiments of the present invention, examples of which are shown in the accompanying drawings. Wherever possible, the same reference numbers will be used throughout the drawings to refer to the same or like parts.

An apparatus is provided for securing a catheter transducer. In accordance with one illustrative embodiment, the apparatus accurately secures the transducer at a desired location, e.g., the phlebostatic axis (midchest), thereby reducing the likelihood of inaccurate measurements due to improper positioning of the transducer. The apparatus further secures the transducer and pressure tubing to help avoid accidental dislodgement of the catheter.

Figure 1:
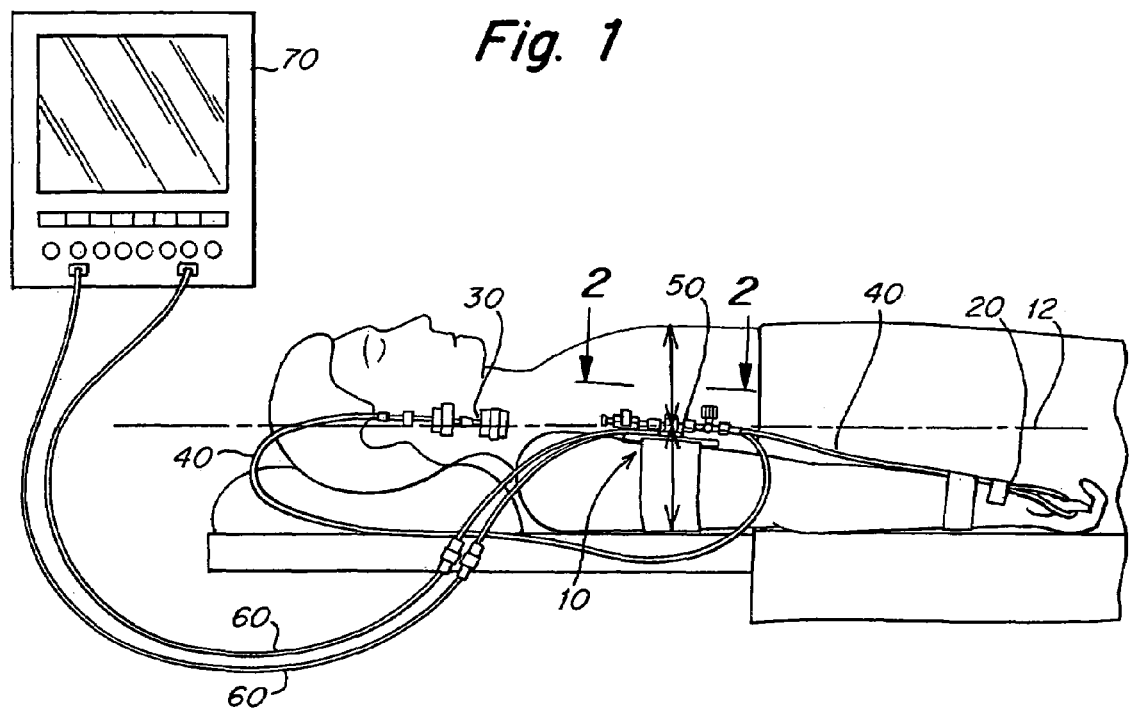
FIG. 1 shows a hemodynamic monitoring system utilizing a transducer holder in accordance with one illustrative embodiment.
Figure 2:
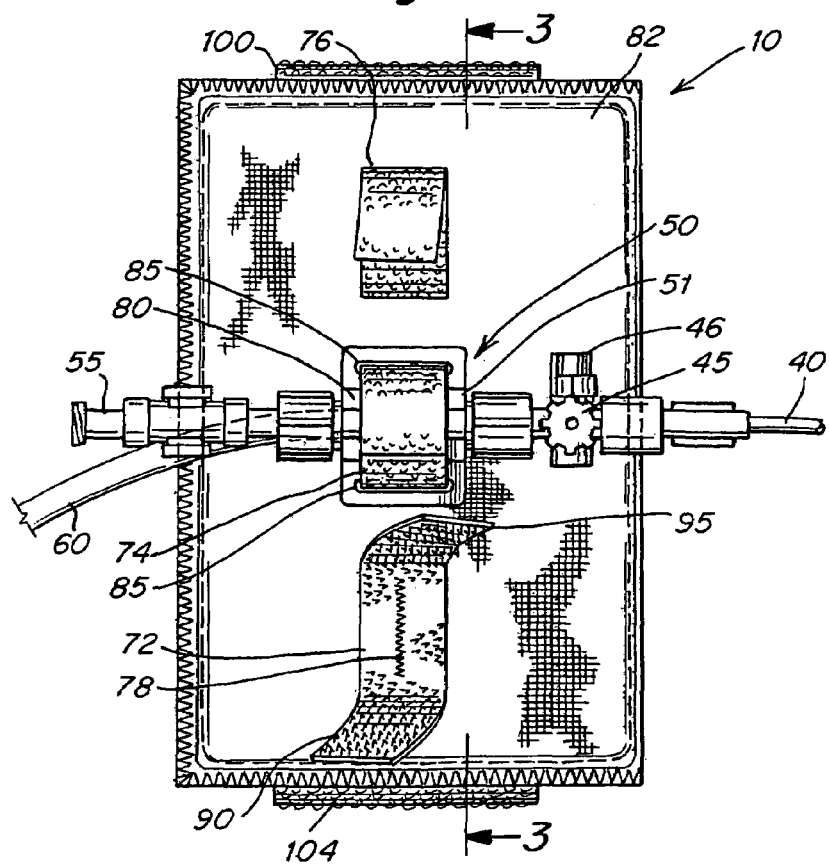
FIG. 2 is a plan view along lines 2-2 of the transducer holder of FIG. 1.

FIG. 1 shows a hemodynamic monitoring system for a patient utilizing a transducer holder 10 in accordance with one illustrative embodiment of the invention, with FIGS. 2-4 showing different views of the holder 10. The system includes a radial artery (RA) catheter 20 and a pulmonary artery (PA) catheter 30 each connected via high-pressure tubing 40 to a transducer assembly 50 held in place by holder 10. Like transducer assemblies 50 are side by side in FIG. 1, thus, only the RA catheter transducer assembly can be seen in FIG. 1. Cabling 60 connects each transducer assembly 50 to hemodynamic monitor 70. The monitor 70 can be used to display the vascular pressure of the patients pulmonary and radial arteries, respectively, sensed by a transducer 51 (FIG. 2) contained in each transducer assembly 50.

As shown in FIG. 1, the holder 10 ensures that the transducer assemblies 50 (and transducers 51) are held at the correct horizontal location, in this case axis 70, which corresponds to the $4^{th}$ intercostal space at the midaxillary line.

FIG. 2 shows a plan view of the holder 10 and the manner in which the holder secures transducer assembly 50. (While there are two pressure transducer assemblies in FIG. 1, one has been removed in FIG. 2 from the holder 10 to illustrate how the assembly 50 is removed.) Pressure transducer 51 includes an electronic sensor to convert a vascular pressure from tubing 40 into an electric signal sent along cable 60 and converted into a readable signal on monitor 70. The pressure transducer 51 is held in a plastic enclosure 80 of the transducer assembly 50.

The catheter tubing 40 is connected to a stopcock 45 which connects the vascular tubing 40 to the transducer 51 to enable pressure sensing. Stopcock 45 closes off tubing 40 so as to be able to expose transducer 51 to air (port 46), for the purpose of zeroing transducer 51. Port 55 is provided for inserting a flush solution.

The transducer holder 10 includes fasteners, such as straps 72, 74 and 76, for the purpose of securing transducer assemblies 50. Although straps are used, any appropriate fastener, such as adhesives, clips, etc., may be used. Each strap is fixedly attached, for example via stitching 78, to a base 82 in a middle section of the strap to form strap ends 90 and 95. Although the straps are shown mounted horizontally across the base 82, the straps (or any other type of fastener) can be mounted in any desired orientation, depending on the position of the patient, procedure being used, etc. To facilitate placing the straps in different orientations and for ease of mounting and removal, the straps could also be attached to the base via a hook and loop mating surfaces.

To assist the caregiver in mounting and removing transducer assemblies 50, straps 72, 74, and 76 can be colored differently. For example, each strap can be colored red, blue, and yellow, respectively, to inform the caregiver of the intracardiac pressure being sensed by each transducer. For example, the colors red, blue, and yellow are used in the industry to indicate arterial lines, central venous lines, and pulmonary lines, respectively. Accordingly, the straps can be colored red, blue, and yellow to inform the caregiver the pressure being sensed by the assembly secured to the strap.

Plastic enclosure 80 of the transducer 50 includes openings 85 which accommodate strap ends 90 and 95. The base 82 is made of a rigid yet bendable material 108, e.g., a soft metal, surrounded by foam layers 112 and 114 on either side. Alternatively, base can be formed of any cloth material by itself, without rigid material 108.

In the foregoing illustrative embodiment, the inner surface 84 of each strap 72, 74 and 76 includes a hook surface for mating with loop surface 86 on the opposite side of the strap. Thus, as seen in FIG. 3, the hook surface of strap end 90 overlaps loop surface of strap end 95 to secure the transducer, or vice versa.

The holder 10 also includes straps 100 and 102 (FIGS. 3 and 4) for securing the holder to a patient's arm or other body area. Straps 100 and 102 include a loop surface 104 to which a hook connector 106 attached to an end of the strap 100 can be used to secure the strap 100 to strap 102, thereby securing the holder to the patient's limb. Alternatively, a single strap having a hook connector could wrap around the patient's limb and reattach to the base 82.

The holder 10 accurately and securely locates the pressure transducers in a desired location and permits easy removal and reattachment if necessary. As shown in the foregoing figures, the transducer holder can accommodate up to three transducers in the foregoing illustrative embodiment, although, clearly, more or less can be used.

Figure 5:
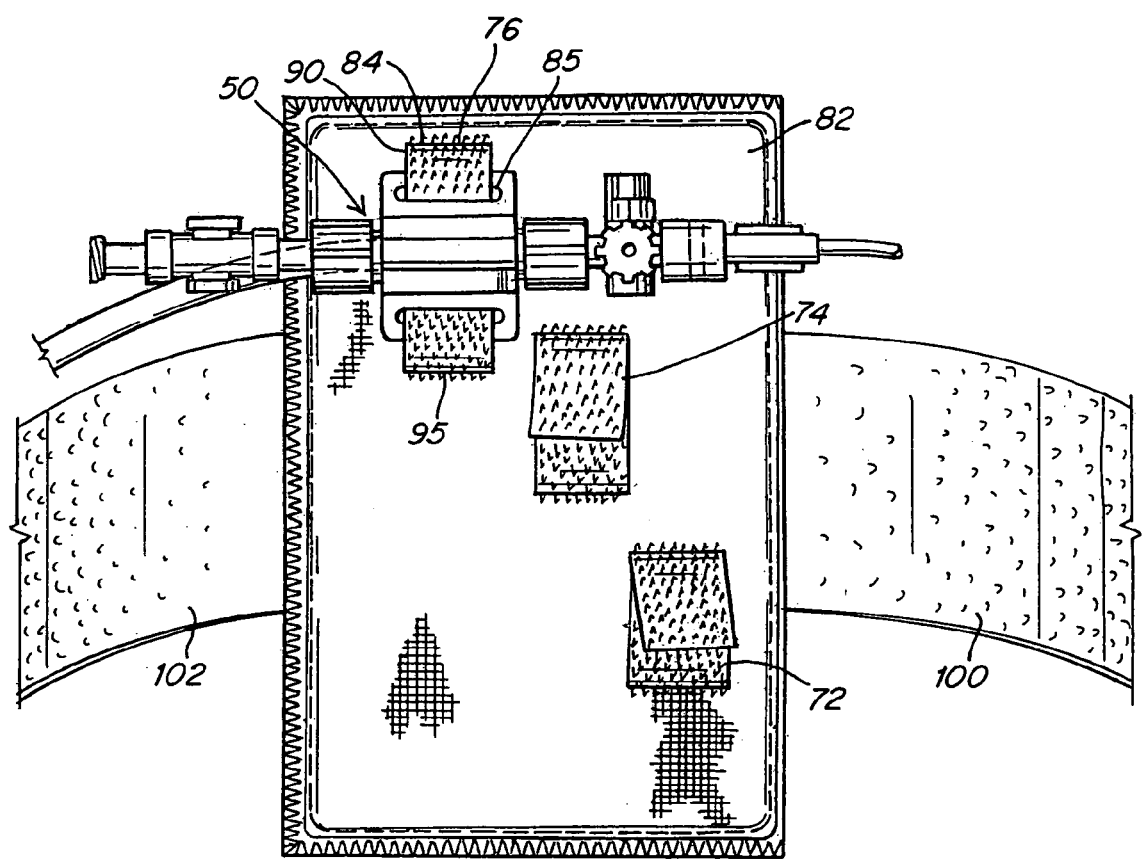
FIG. 5 is a perspective view of a transducer holder in accordance with another illustrative embodiment.

FIG. 5 shows another illustrative embodiment of a transducer holder 10. In this embodiment, straps 100 and 102 have been attached to wider sides of base 82 such that transducer assembly 50 is oriented substantially perpendicular to the patient's arm when attached, as opposed to substantially parallel in the previous embodiment. Furthermore, fastener straps 72, 74, and 76 are reversed such that hook surface 84 is attached to and faces base 82, and loop surface 86 faces away from base 82. Thus, as shown in FIG. 5, ends 90 and 95 reattach to loop surface of base 82 after being threaded through openings 85 of transducer enclosure 80. This conveniently enables a caregiver to view the transducer. Because attaching the straps 72, 74, and 76 in this manner uses more space on the surface of base 82, the straps are staggered with respect to one another to enable the ends of the straps to attach to the base.

Other embodiments of the invention will be apparent to those skilled in the art from consideration of the specification and practice of the invention disclosed herein. For example, instead of hook and loop fasteners, other fastening means could be used, such as adhesives, clips, etc., for both securing the transducer assembly, and for attaching the holder to the patient's limb. It is intended that the specification and examples be considered as exemplary only, with a true scope and spirit of the invention being indicated by the following claims.

What is claimed is:

1. A transducer holding system comprising:
    a base;
    a transducer assembly including a transducer and having first and second openings on either side of the transducer;
    two or more fasteners arranged on the base, each fastener for securing the transducer assembly to the base, each fastener fixedly attached to the base at a central location on the fastener between the first and second ends of the fastener, wherein the transducer assembly is secured to the base by threading the first and second ends through openings in the transducer assembly and attaching the first end to the second end thereby substantially surrounding and securing the transducer in place; and
    at least one strap attached to the base for securing the base to the patient, wherein at least two of the two or more fasteners have a different color from one another.

2. The transducer holding system according to claim 1, wherein hook material on the first end secures the transducer by attaching to loop material on the second end.

3. The transducer holding system according to claim 1, wherein the at least one strap includes first and second straps attached to the base adapted to secure the base to a patient's arm.

4. The transducer holding system according to claim 3, wherein the first and second straps secure the transducer holder by the first and second straps wrapping around the patient's arm and the first strap attaching to the second strap.

5. The transducer holding system according to claim 4, wherein the first strap includes a hook fastener for adhering to loop material on the second strap.

6. The transducer holding system according to claim 1, wherein the two or more fasteners include three fasteners, and the three fasteners are colored blue, red, and yellow to indicate the pressure being sensed by the transducer secured thereby.

* * * * *